United States Patent [19]

Hotten

[11] 4,225,712

[45] Sep. 30, 1980

[54] TETRAHYDROPYRIMIDYL-SUBSTITUTED COMPOUNDS

[75] Inventor: Bruce W. Hotten, Orinda, Calif.

[73] Assignee: Chevron Research Company, San Francisco, Calif.

[21] Appl. No.: 920,436

[22] Filed: Jun. 29, 1978

Related U.S. Application Data

[60] Division of Ser. No. 845,700, Oct. 26, 1977, which is a continuation-in-part of Ser. No. 610,761, Sep. 8, 1975, abandoned, which is a continuation-in-part of Ser. No. 431,831, Jan. 7, 1974, abandoned.

[51] Int. Cl.$^2$ .......................................... C07D 403/14
[52] U.S. Cl. .................................................... 544/296
[58] Field of Search ......................................... 544/296

[56] References Cited

U.S. PATENT DOCUMENTS

| | | | |
|---|---|---|---|
| 2,830,019 | 4/1958 | Fields et al. | 252/51.5 A |
| 2,844,446 | 7/1958 | Cyba et al. | 252/34 |
| 3,235,548 | 2/1966 | Pollack et al. | 544/296 |

*Primary Examiner*—Paul M. Coughlan, Jr.
*Attorney, Agent, or Firm*—D. A. Newell; J. J. DeYoung

[57] ABSTRACT

A new class of compositions, tetrahydropyrimidyl-substituted compounds, useful as ashless bases and rust inhibitors, is prepared by reacting a $C_3$-to $C_{50}$ amine containing a 1,3-diaminopropane group with ethylenediamine tetraacetic acid or nitrilotriacetic acid at a temperature of 150° to 250° C. for 10 to 100 hours.

4 Claims, No Drawings

TETRAHYDROPYRIMIDYL-SUBSTITUTED COMPOUNDS

CROSS-REFERENCE TO RELATED APPLICATIONS

This application is a Division of application Ser. No. 845,700 filed Oct. 26, 1977 which, in turn, is a Continuation-in-Part of application, Ser. No. 610,761 filed Sept. 8, 1975, now abandoned, which, in turn, is a Continuation-in-Part of application Ser. No. 431,831, filed Jan. 7, 1974, now abandoned.

BACKGROUND OF THE INVENTION

Varnish, sludge, rust and corrosion seriously reduce the efficiency of an internal combustion engine by clogging restricted openings and reducing the clearance of moving parts. A high-quality motor lubricating oil must incorporate detergents capable of controlling varnish formation and corrosion. This function has heretofore been mainly performed by certain metallo-organic salts and bases in the lubricating composition. However, the present trend to unleaded fuels and ashless lubricating compositions brought about by certain important environmental concerns necessitates the search for non-metallic (ashless) substitutes for the metallo-organic detergents. These non-metallics must fulfill a host of requirements, primary among which are basicity and thermal stability.

DESCRIPTION OF THE PRIOR ART

U.S. Pat. No. 2,844,446 discloses bis-tetrahydropyrimidines wherein the rings are joined by a hydrocarbon radical of at least 2 carbon atoms. The bis-tetrahydropyrimidines are prepared by condensing 2 mols of an alkaline polyamine having at least 1 primary amino group separated from another primary or secondary amino group by 3 carbon atoms with 1 mol of a dicarboxylic acid at a temperature above 175° C. 1,3-Propylenediamine is disclosed as a suitable amine. Suitable polycarboxylic acids include oxalic, glutaric, adipic, higher polybasic carboxylic acids, and the like. The bis-tetrahydropyrimidines of this invention are useful in hydrocarbon distillates for retarding or preventing discoloration, oxidation, rust or corrosion, and in addition to impart detergent properties. In lubricating oils, the additive may function as a pour-point depressant, viscosity-index improver, etc.

U.S. Pat. No. 3,325,496 teaches the use of triaminopyrimidines as high-temperature lubricant fluids.

U.S. Pat. No. 2,830,019 teaches the production of amine salts from the reaction of an aliphatic or heterocyclic amine with a nitrogen-containing polycarboxylic acis such as ethylenediamine tetraacetic acid.

SUMMARY OF THE INVENTION

It has been discovered that tetrahydropyrimidyl-substituted compounds prepared from a $C_3$ to $C_{50}$ amine containing a 1,3-diaminopropane group and ethylenediamine tetraacetic acid (EDTA) or nitrilotriacetic acid (NTA) are exceptionally superior ashless base additives for lubricating oil having good thermal stability as well as basicity.

DETAILED DESCRIPTION OF PREFERRED EMBODIMENTS

The tetrahydropyrimidyl-substituted compounds of this invention are prepared by reacting ethylenediamine tetraacetic acid or nitrilotriacetic acid with a compound of Formula I:

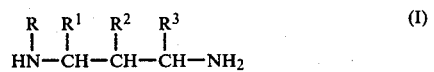

wherein each of R, $R^1$, $R^2$ and $R^3$ is independently hydrogen or hydrocarbyl. The reaction is carried out at a temperature of 150° to 250° C. for 10 to 100 hours. The reaction product may be used directly in the lubricating compositions of this invention, or it may be purified by methods well known in the art to substantially isolate the primary polytetrahydropyrimidine product. In generally, the use of the reaction product per se is preferred.

The compositions of this invention are found to function as superior ashless additives for lubricating oil compositions in that they retain substantial alkalinity values under conditions of sustained high temperatures and they are highly rust-inhibitory.

The products of this invention are composed of compounds of the following formulas, wherein Formula II representes the primary product from the reaction of nitrilotriacetic acid with the 1,3-diaminopropane compound of Formula I. Formula III represents the primary product from the reaction of ethylenediamine tetraacetic acid with the 1,3-diaminopropane compound of Formula I.

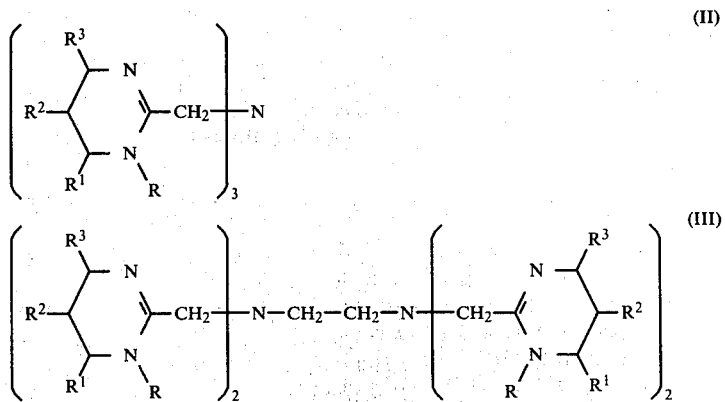

In the above formulas, each of R, R¹, R² and R³ is hydrogen or hydrocarbyl. As used herein, hydrocarbyl represents a radical composed primarily of carbon and hydrogen and containing from 1 to about 50 carbon atoms per hydrocarbyl group. The hydrocarbyl group is preferably saturated; however it may contain 1 or 2 sites of olefinic unsaturation. Preferably the hydrocarbyl group is an alkyl group of from 1 to 30 carbon atoms, and more preferably of from 1 to 20 carbon atoms. Suitable substituents include methyl, hexadecyl, tetrapropenyl, hexabutenyl, ethylbenzyl, and the like. Without altering the basic performance characteristics of the compositions of this invention, each of R, R¹, R² and R³ can be a hydrocarbyl group which is substituted by 1 to 2 alkylamino, alkyloxy or hydroxyalkyl groups, e.g., ethylamino, hydroxyethyl, ethyloxy, and the like. Preferred compositions are those prepared from an N-substituted 1,3-diaminopropane, i.e., those compounds wherein R is hydrocarbyl and R¹, R² and R³ are each hydrogen. The preparation of the compositions of this invention is carried out by mixing EDTA or NTA and the amine in a suitable solvent, such as xylene, while maintaining the temperature at about 150° to 250° C. for about 10 to about 100 hours, preferably from about 20 to about 40 hours. The reaction temperature is, of course, generally limited by the reflux temperature of this solvent or the decomposition temperature of the reactants or product. It is preferred to react all of the carboxylic acid groups; therefore it is preferred to operate with an excess of amine over the stoichiometric requirement. Broadly, from 0.9 to 3 mols of amine per carboxylic acid group is utilized, and preferably 1.5 to 2 mols. The product is complex, containing intermediate amides and other compounds in addition to mixed tetrahydropyrimidino compounds.

EXAMPLES

The preparation of illustrative compositions in the scope of this invention is illustrated by the following examples. It is not intended that these examples represent limitations on the embodiments of this invention.

EXAMPLE 1

Into 600 ml of xylene were placed 57 g (about 0.3 mol) of nitriloacetic acid and 360 g (about 0.9 mol) of N-oleyl-1,3-diaminopropane. The mixtures was held at about 150°-200° C. for about 27 hours and a total of 30 ml of water was evolved (calculated, 35 ml). The 431 g of product had 7.4 weight percent of nitrogen and an alkalinity value of 160 mg KOH/g. The infrared specturm showed the strong C=N band at 1640 cm⁻¹, and nuclear magnetic resonance (NMR) confirmed the presence of the methylene-ring hydrogens of the tetrahydropyrimidinyl group.

EXAMPLE 2

N-oleyl-1,3-diaminopropane (2400 g, about 6 mols) and nitrilotriacetic acid (282 g, about 2 mols) were mixed under nitrogen with stirring to 200° C. over a 2-hour period. The mixture was maintained at this temperature for about 18 hours, stripped under vacuum and nitrogen to 150° C., and 2661 g of product was recovered having an alkalinity value of 176 mg KOH/g. The product is tris-(3-oleyl-3,4,5,6-tetrahydro-2-pyrimidylmethyl)amine with some intermediate amides.

EXAMPLE 3

Into 300 ml of xylene were mixed 146 g of ethylenediamine tetraacetic acid (about 0.5 mol) and 800 g of N-oleyl-1,3-diaminopropane. The mixture was heated at 150°-200° C. for about 48 hours, and 69 ml of water was evolved (72 ml calculated). The 904 g of product had an alkalinity value of 180 mg KOH/g and showed the infrared absorption at 1630 cm⁻¹ typical of C=N. The product is N,N,N',N'-tetrakis-(3-oleyl-3,4,5,6-tetrahydro-2-pyrimidylmethyl) ethylenediamine, mixed with some amido intermediates.

EXAMPLE 4

In 100 ml of xylene were mixed 56 g (about 0.29 mol) of nitrilotriacetic acid and 212 g (about 0.88 mol) of N-tallow-alkyl-1,3-diaminopropane. The mixture was heated to about 200° C. for about 27 hours. 31 ml of water was evolved (31 ml calculated). The 330 g of product contained an infrared absorption at 1640cm⁻¹. The product is tris-(3-tallowyl-3,4,5,6-tetrahydro-2-pyrimidylmethyl)amine with some amido intermediates.

EXAMPLE 5

The 20 ml of xylene were added 191 g (about 1 mol) of nitrilotriacetic acid and 834 g (about 3 mols) of N-coco alkyl-1,3-diaminopropane. The mixture was heated for about 29 hours at about 200° C. 101 ml of water evolved (108 ml calculated). The 911 g of product had an alkalinity value of 187 and contained 3.5 weight percent of nitrogen. The product contained a sharp infrared absorption at 1630 cm⁻¹. It is tris-(3-coco-2,4,5,6-tetrahydro-2-pyrimidylmethyl)amine.

Evaluation

The polytetrahydropyrimidinyl products prepared by the process of this invention display satisfactory anti-varnish detergency as additives in lubricating oils for the internal combustion engine as illustrated in the Ford V* varnish test results of Table I. In this test, a Ford V8 engine of 302 cubic inches displacement is operated in cycles of 500/2500/2500 rpm for periods of 45/120/75 minutes on a Chevron gasoline containing FCC heavy fraction (i.e., product of fluidized-bed catalyst cracking.

TABLE I

| Ashless Base in Ford V8 Varnish Test | | | | |
|---|---|---|---|---|
| | Varnish Rating at (hours) | | | |
| | 20 | 40 | 60 | 80 |
| No base[1] | 8.9 | 8.0 | <7.7 | — |
| Metallic base[2] | 9.7[4] | 9.4 | 9.1[4] | 8.8[4] |
| Polytetrahydropyrimidine[3] | 9.6 | 8.9 | 8.7 | 8.3 |

[1]All oils contained 6 weight percent polyisobutenyl succinimide of tetraethylene pentamine and 15 mM/kg of zinc dialkyldithiophosphate in a neutral petroleum oil.
[2]30 mM/kg of carbonated, sulfurized, calcium polypropylene phenate (9.25% calcium) and 30 mM/kg of overbased calcium sulfonate (11.4% calcium).
[3]Tris-(3-oleyl-3,4,5,6-tetrahydro-2-pyrimidylmethyl)amine at 2 weight percent (63 meg/kg).
[4]Mean value of two runs.

In the Ford V8 varnish test, the engine is disassembled at 20-hour intervals and the piston varnish is measured on a scale of 0–10, with 10 being completely clean. The polytetrahydropyrimidine ashless base is found to give anti-varnish protection which is comparably satisfactory to the metallic base-containing, e.g., overbased, lubricating oil compositions in present use.

The polytetrahydropyrimidines display excellent rust-inhibitory ability in the ASTM D1748 Humidity Cabinet Rust Test. In Table II, various low-ash and ashless lubricating oil compositions have been tested in the Humidity Cabinet Rust Test with and without the addition of 1% by weight of the product of Example 1.

TABLE II

Rust Inhibition of Polytetrahydropyrimidine (1%)

| Composition | Humidity Cabinet Rust Life (hours) | |
|---|---|---|
| | Without | With |
| Low-Ash[1] | <24 | (50) |
| Low-Ash[2] | <24 | (90) |
| Ashless[3] | 24 | (800) |
| Ashless[4] | 40 | (700) |
| Ashless[5] | 130 | (>2000) |

[1] 6 weight percent of polyisobutenyl succinimide of tetraethylpentamine and 18 mM/kg of zinc dialkyl dithiophosphate.
[2] The composition of Footnote 1 + 0.2 weight percent of tetrapropenylsuccinic acid.
[3] 5 weight percent of polyisobutenylsuccinimide of triethylenetetraamine, 1 weight percent of diisobornyldiphenylamine and 1% of bisalkylphenol sulfide.
[4] The composition of Footnote 3 + 0.2 weight percent of tetrapropenylsuccinic acid.
[5] 6 weight percent polyisobutenylsuccinimide of tetraethylenepentamine, 1 weight percent sulfurized wax, 3 weight percent sulfurized alkylphenol and 1.5 weight percent hindered bisphenol (Ethyl 702).

The humidity cabinet rust lifetime in hours for the same composition containing 1% of the polytetrahydropyrimidines is given in parentheses in Table II. Even the low-ash and ashless compositions containing tetrapropenylsuccinic acid are found to be improved in rust inhibition by the addition of only 1% of the polytetrahydropyrimidine.

TABLE III

Rust Inhibition of Polytetrahydropyrimidine

| Additive at 1% | Humidity Cabinet Rust Life (Hours) |
|---|---|
| None[1] | <24 |
| Example 2 | 300 |
| Example 4 | 270 |
| Example 5 | 200 |
| Example 3 | 250 |

[1] A neutral petroleum oil of about 480 SUS at 100° F.

The rust-inhibitory power of the polytetrahydropyrimidines of Examples 2-5 is demonstrated in the Table III.

The alkalinity value (AV) of a base is an important indicator of the ability of the additives to inhibit corrosion, varnish formation and rust. The alkalinity value is obtained by titrating the material with perchloric acid in glacial acetic acid. The results are converted to mg KOH/g necessary to neutralize the titrated acid. Just as important as a high alkalinity value in a lubricating composition is the ability of the base to maintain its AV over a period of time under the extreme thermal conditions encountered in actual use.

TABLE IV

Thermal Stability

| Additive[1] | Initial Alkalinity Value (AV) | Retention |
|---|---|---|
| Polyisobutenyl succinimide of tetraethylene pentamine | 9.1 | 67% |
| Polyisobutenyl ethylenediamine | 4.4 | 25% |
| Example 2 | 16 | 72% |
| Example 4 | 17 | 79% |

[1] All additives are at 10 weight percent in a neutral mineral oil.

The results of Table IV illustrate the outstanding thermal stability of the polytetrahydropyrimidines in comparison with other ashless bases. Lubricating oil compositions containing a neutral mineral oil and 10% of the additive in Table IV were maintained at 300° F. for 24 hours. The initial and final AV was measured and the result expressed as a percent retention of AV under these conditions. The polytetrahydropyrimidines display an outstanding retention of alkalinity value.

Prior Art Example

The example taught at Col. 5, lines 4-11, of U.S. Pat. No. 2,830,019 was substantially repeated as follows:

Into a 1-liter flask were placed 251.3 g (0.86 mol) of ethylenediamine tetraacetic acid and 166.1 g (0.46 mols) of Duomeen S. The mixture was stirred and heated to 155° C. for 20 minutes. The reaction product was solid and was insoluble in oil. IR, NMR and UV analyses indicated a product consisting primarily of amides with some salts. The rust-inhibitory ability of the product was tested using ASTM D1748 Humidity Cabinet Rust Test as in Table II above. The humidity cabinet rust life was less than 24 hours.

Additive Medium

The products of this invention may be used singly or in combinations of two or more in an oil of lubricating viscosity. The lubricating oil can be any relatively inert and stable fluid of lubricating viscosity. Such lubricating fluids are generally of viscosities of 35-50,000 Saybolt Universal Seconds (SUS) at 100° F. (37° C.). The fluid medium or oil may be derived from either natural or synthetic sources. Included among the natural hydrocarbonaceous oils are paraffin-base, naphthenic-base or mixed-base oils. Synthetic oils include polymers of various olefins, generally of from 2 to 6 carbon atoms, alkylated aromatic hydrocarbons, etc. Non-hydrocarbon oils include carboxylic acid esters, polyalkylene oxides, phosphates, aromatic ethers, silicones, etc. The preferred lubricating media are the hydrocarbonaceous media, both natural and synthetic. Preferred are those hydrocarbonaceous oils having viscosities of about 100-4000 SUS, and particularly those having viscosities of from 200 to about 2000 SUS at 100° F. The lubricating fluids may be used individually or in combinations when intermiscible or made so by the use of mutual solvents.

The lubricating oil will be present at 75 or greater percent by weight of the final composition. In concentrates, however, the oil may be present at 1-84%, preferably 1-50%, by weight. These concentrates are diluted with additional oil prior to being placed in service to obtain the requisite concentration.

Other additives may also be present in the compositions of this invention. Materials may be added for enhancing the EP properties of the composition, or providing other desirable properties to the lubricating medium. These include such additives as rust and corrosion inhibitors, anti-oxidants, oiliness agents, detergents, rust inhibitors, the viscosity-index improvers, pour-point depressants, etc. Usually these will be in the range of from about 0-5%, more generally in the range of from about 0-2%, of the total composition. Typical additional additives found in compositions of the present invention include phenolic and arylamine antioxidants and ashless dispersents such as the alkenylsuccinimides. The polytetrahydropyrimidines of the present invention may find use in lubricating compositions containing ash such as the metallo-organic detergents which are known in the art, e.g., the alkaline earth phenates or sulfonates.

The additives of the present invention will generally be present in lubricating oils in functional amounts consistent with their use as ashless bases and rust inhibitors. Such functional amounts will generally range from about 0.05 to 15 weight percent of the total composition, more usually in the amount of about 0.1 to about 10 weight percent of the total composition.

What is claimed is:

1. A compound of the formula

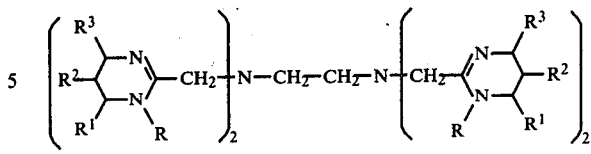

wherein $R$, $R^1$, $R^2$ and $R^3$ are independently hydrogen or radicals composed primarily of carbon and hydrogen and containing from 1 to about 50 carbon atoms.

2. The compound of claim 1 wherein $R$ is a radical composed primarily of carbon and hydrogen and containing from 1 to about 50 carbon atoms and $R^1$, $R^2$ and $R^3$ are hydrogen.

3. The compound of claim 2 wherein $R$ is an alkyl group of 1 to 20 carbon atoms.

4. The compound of claim 2 wherein $R$ is selected from oleyl, tallow and coco groups.

* * * * *